United States Patent
Johnson

(10) Patent No.: US 7,192,959 B2
(45) Date of Patent: Mar. 20, 2007

(54) SODIUM CHANNEL BLOCKERS

(75) Inventor: Michael R. Johnson, Chapel Hill, NC (US)

(73) Assignee: Parion Sciences, Inc., Durham, NC (US)

(*) Notice: Subject to any disclaimer, the term of this patent is extended or adjusted under 35 U.S.C. 154(b) by 500 days.

(21) Appl. No.: 10/828,353

(22) Filed: Apr. 21, 2004

(65) Prior Publication Data

US 2004/0198746 A1 Oct. 7, 2004

Related U.S. Application Data

(62) Division of application No. 10/076,551, filed on Feb. 19, 2002, now Pat. No. 6,858,614.

(51) Int. Cl.
A01N 43/66 (2006.01)
A61K 31/53 (2006.01)
C07D 253/00 (2006.01)
C07D 251/00 (2006.01)

(52) U.S. Cl. ............ 514/241; 514/242; 544/182; 544/219

(58) Field of Classification Search .......... None
See application file for complete search history.

(56) References Cited

U.S. PATENT DOCUMENTS

| 3,313,813 | A | 4/1967 | Cragoe, Jr. et al. |
| 3,472,848 | A | 10/1969 | Cragoe, Jr. et al. |
| 3,544,571 | A | 12/1970 | Cragoe, Jr. et al. |
| 3,625,950 | A | 12/1971 | Cragoe, Jr. |
| 3,668,241 | A | 6/1972 | Cragoe, Jr. et al. |
| 3,794,734 | A | 2/1974 | Cragoe, Jr. et al. |

(Continued)

FOREIGN PATENT DOCUMENTS

WO  WO 01/05773 A1  1/2001

OTHER PUBLICATIONS

Velly et al, "Effects of amiloride and its analogues on [3H]batrachotoxinin-A 20-α benzoate binding, [3H]tetracaine binding and 22 Na influx" European Journal of Pharmacology, vol. 149, No. 1-2, 1988, pp. 97-105.*

(Continued)

Primary Examiner—Zachary C. Tucker
(74) Attorney, Agent, or Firm—Oblon, Spivak, McClelland, Maier & Neustadt, P.C.

(57) ABSTRACT

The present invention relates to compounds represented by formula (I):

(I)

in which at least one of $R^3$ and $R^4$ is a group represented by formula (A):

(A)

where the structural variables are defined herein. The compounds are useful for blocking sodium channels.

34 Claims, 2 Drawing Sheets

Effect of compound V on ovine mucociliary clearance

■ Vehicle
▲ V

Note: A decrease in % retention equals enhanced MCC

U.S. PATENT DOCUMENTS

| | | |
|---|---|---|
| 3,864,401 A | 2/1975 | Schultz et al. |
| 3,894,065 A | 7/1975 | Cragoe, Jr. et al. |
| 3,914,253 A | 10/1975 | Cragoe, Jr. et al. |
| 3,928,624 A | 12/1975 | Cragoe, Jr. et al. |
| 3,929,872 A | 12/1975 | Cragoe, Jr. et al. |
| 3,931,239 A | 1/1976 | Cragoe, Jr. et al. |
| 3,953,476 A | 4/1976 | Cragoe, Jr. et al. |
| 3,956,374 A | 5/1976 | Shepard et al. |
| 3,958,004 A | 5/1976 | Cragoe, Jr. et al. |
| 3,966,966 A | 6/1976 | Cragoe, Jr. et al. |
| 3,974,212 A | 8/1976 | Cragoe, Jr. et al. |
| 3,976,681 A | 8/1976 | Cragoe, Jr. et al. |
| 3,976,686 A | 8/1976 | Cragoe, Jr. et al. |
| 3,979,361 A | 9/1976 | Schultz et al. |
| 3,984,465 A | 10/1976 | Cragoe, Jr. et al. |
| 3,984,552 A | 10/1976 | Cragoe, Jr. et al. |
| 3,987,091 A | 10/1976 | Cragoe, Jr. et al. |
| 3,989,749 A | 11/1976 | Cragoe, Jr. et al. |
| 3,991,087 A | 11/1976 | Cragoe, Jr. et al. |
| 3,991,106 A | 11/1976 | Cragoe, Jr. et al. |
| 4,003,927 A | 1/1977 | Woltersdorf, Jr. et al. |
| 4,006,180 A | 2/1977 | Cragoe, Jr. et al. |
| 4,012,524 A | 3/1977 | Cragoe, Jr. et al. |
| 4,025,625 A | 5/1977 | Rooney et al. |
| 4,067,980 A | 1/1978 | Cragoe, Jr. et al. |
| 4,085,117 A | 4/1978 | Cragoe, Jr. et al. |
| 4,085,211 A | 4/1978 | Cragoe, Jr. et al. |
| 4,085,219 A | 4/1978 | Cragoe, Jr. et al. |
| 4,087,526 A | 5/1978 | Cragoe, Jr. et al. |
| 4,087,542 A | 5/1978 | Cragoe, Jr. et al. |
| 4,092,414 A | 5/1978 | Cragoe, Jr. et al. |
| 4,100,294 A | 7/1978 | Cragoe, Jr. et al. |
| 4,105,769 A | 8/1978 | Rooney et al. |
| 4,140,776 A | 2/1979 | Cragoe, Jr. et al. |
| 4,145,551 A | 3/1979 | Cragoe, Jr. et al. |
| 4,159,279 A | 6/1979 | Smith et al. |
| 4,163,781 A | 8/1979 | Cragoe, Jr. et al. |
| 4,163,794 A | 8/1979 | Cragoe, Jr. et al. |
| 4,177,285 A | 12/1979 | Cragoe, Jr. et al. |
| 4,181,727 A | 1/1980 | Cragoe, Jr. et al. |
| 4,196,292 A | 4/1980 | Woltersdorf, Jr. et al. |
| 4,237,130 A | 12/1980 | Cragoe, Jr. et al. |
| 4,237,144 A | 12/1980 | Cragoe, Jr. et al. |
| 4,246,406 A | 1/1981 | Cragoe, Jr. et al. |
| 4,277,602 A | 7/1981 | Woltersdorf et al. |
| 4,291,050 A | 9/1981 | Woltersdorf, Jr. et al. |
| 4,296,122 A | 10/1981 | Cragoe, Jr. et al. |
| 4,298,743 A | 11/1981 | Cragoe, Jr. et al. |
| 4,317,822 A | 3/1982 | Woltersdorf, Jr. et al. |
| 4,362,724 A | 12/1982 | Bock et al. |
| 4,401,669 A | 8/1983 | Cragoe, Jr. et al. |
| 6,475,509 B1 * | 11/2002 | Boucher, Jr. ............... 424/434 |

OTHER PUBLICATIONS

Kellerman, D. "P2Y2 Receptor Agonists. A New Class of Medication Targeted at Improved Mucociliary Clearance" Chest, vol. 121(5), supplement, pp. 201S-205S.*

R. Tarran et al., The CF Salt Controversy: In Vivo Observations and Therapeutic Approaches, *Molecular Cell*, vol. 8, 149-158, Jul. 2001.

Michael R. Knowles et al., Amiloride in Cystic Fibrosis: Safety, Pharmacokinetics, and Efficacy in the Treatment of Pulmonary Disease, Chapter 20, p. 301-316, 1992.

Louis Simchowitz et al., An Overview of the Structure Activity Relations in the Amiloride Series, Chapter 2, p. 9-25, 1992.

J.R. Sabater et al., Aerosolization of P2y2-Receptor Agonists Enhances Mucociliary Clearance in Sheep, *The American Physiological Society*, p. 2191-2196, 1999.

Thomas R. Kleyman et al., Amiloride and Its Analogs as Tools In the Study of Ion Transport, *The Journal of Membrane Biology*, vol. 105, pp. 1-21, 1988.

Edward C. Taylor et al., A Facile Route to "Open Chain" Analogues of DDATHF, *Heterocycles*, vol. 28, No. 2, 1989.

Paul-Michael Windscheif et al., Substituted Dipyridlethenes and -ethynes and Key Pyridine Building Blocks, *Synthesis*, pp. 87-92, Jan. 1994.

Edward J. Cragoe, Jr., The Synthesis of Amiloride and Its Analogs, p. 24-38, Chapter 3, 1992.

Jack H. Li, et al., Stereoselective Blockage of Amphibian Epithelial Sodium Channels by Amiloride Analogs, *The Journal of Pharmacology and Experimental Therapeutics*, vol. 267, No. 3, pp. 1081-1084, 1993.

Pallav L. Shah, M.D., Chapter 7, Progress in the Treatment of Pulmonary Disease in Cystic Fibrosis, Annual Reports in Medicinal Chemistry, vol. 36, pp. 67-76, 2001.

Dieter Worlitzsch et al., Effects of Reduced Mucus Oxygen Concentration in Airway Pseudomonas Infections of Cystic Fibrosis Patients, *The Journal of Clinical Investigation*, Feb. 2002, vol. 109, No. 3, pp. 317-336.

Edward J. Cragoe, Jr., et al., Chapter 7: Diuretic Agents, *Annual Reports in Medicinal Chemistry*, 1966, p. 59-68.

Edward J. Cragoe, Jr., et al., Chapter 7: Diuretic Agents, *Annual Reports in Medicinal Chemistry*, 1965, p. 67-77.

Robert L. Smith, et al., Chapter 8: Diuretics, *Annual Reports in Medicinal Chemistry*, vol. 11, pp. 71-79, 1976.

Robert L. Smith, et al., Chapter 7: Diuretics, *Annual Reports in Medicinal Chemistry*, vol. 13, pp. 61-70, 1978.

Edward J. Cragoe, Jr., Structure-Activity Relationships in the Amiloride Series, *Merck Sharp and Dohme Research Laboratories*, 1979, pp. 1-20.

T.M. Cocks, et al., British Journal of Pharmacology, 95(1), pp. 67-76 (English) 1988.

Thomas R. Kleyman, et al., American Journal of Physiology, 260(2, Pt.1), pp. C271-C276 (English), 1991.

K.E. Barrett, et al., Annu. Rev. Physiol. 2000; 62, pp. 535-572.

R.F. Epand, et al., British Journal of Cancer, 63(2), 247-51 (English) 1991.

* cited by examiner

Note: A decrease in % retention equals enhanced MCC

SODIUM CHANNEL BLOCKERS

CONTINUING APPLICATION DATA

This application is a Divisional of application Ser. No. 10/076,551, filed on Feb. 19, 2002, now U.S. Pat. No. 6,858,614. That application is incorporated herein by reference.

BACKGROUND OF THE INVENTION

1. Field of the Invention

The present invention relates to sodium channel blockers. The present invention also includes a variety of methods of treatment using these inventive sodium channel blockers.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and one the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete $Cl^-$ (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

SUMMARY OF THE INVENTION

It is an object of the present invention to provide compounds that are more potent and/or absorbed less rapidly from mucosal surfaces, and/or are less reversible as compared to known compounds.

It is another aspect of the present invention to provide compounds of formula (I) that are more potent and/or absorbed less rapidly and/or exhibit less reversibility, as compared to compounds such as amilorde, benzamil, and phenamil. Therefore, the compounds of formula (I) will give a prolonged pharmacodynamic half-life on mucosal surfaces as compared to known compounds.

It is another object of the present invention to provide compounds of formula (I) which are (1) absorbed less rapidly from mucosal surfaces, especially airway surfaces, as compared to known compounds and; (2) when absorbed from mucosal surfaces after administration to the mucosal surfaces, are converted in vivo into metabolic derivatives thereof which have reduced efficacy in blocking sodium channels as compared to the administered parent compound.

It is another object of the present invention to provide compounds of formula (I) that are more potent and/or absorbed less rapidly and/or exhibit less reversibility, as compared to compounds such as amiloride, benzamil, and phenamil. Therefore, the compounds of formula (I) will give a prolonged pharmacodynamic half-life on mucosal surfaces as compared to previous compounds.

It is another object of the present invention to provide methods of treatment which take advantage of the properties described above.

The objects of the present invention may be accomplished with a class of pyrazinoylguanidine compounds represented by a compound represented by formula (I):

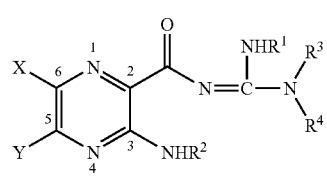

(I)

wherein

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R^2)_2$;

$R^1$ is hydrogen or lower alkyl;

each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

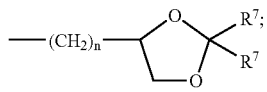

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower alkoxyphenyl)-lower alkyl, naphthyl-lower alkyl, or pyridyl-lower alkyl, with the proviso that at least one of $R^3$ and $R^4$ is a group represented by formula (A):

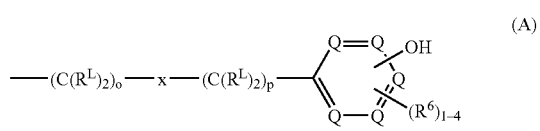

(A)

wherein each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_n-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose, or

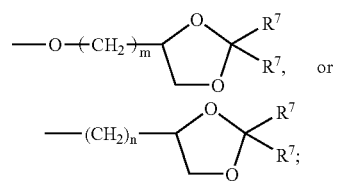

each x is, independently, O, $NR^7$, C=O, CHOH, C=N—$R^6$, or represents a single bond;

each o is, independently, an integer from 0 to 10;

each p is, independently, an integer from 0 to 10;

with the proviso that (a) the sum of o and p in each contiguous chain is from 1 to 10 when x is O, $NR^7$, C=O, or C=N—R⁶ or (b) that the sum of o and p in each contiguous chain is from 4 to 10 when x represents a single bond;

each $R^6$ is, independently, —$R^7$, —OH, —$OR^{11}$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n$(CHOR$^8$)(CHOR$^8$)$_n$—$CH_2OR^8$, —O—$(CH_2)_m$(CHOR$^8$)(CHOR$^8$)$_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2$(CHOR$^8$)(CHOR$^8$)$_n$—$CH_2OR^8$, —O—$(CH_2)_m$—$NR^{10}$—$CH_2$(CHOR$^8$)(CHOR$^8$)$_n$—$CH_2OR^8$, —$(CH_2)_n$—$CO_2R^7$, —O—$(CH_2)_m$—$CO_2R^7$, —$OSO_3H$, O-glucuronide, O-glucose,

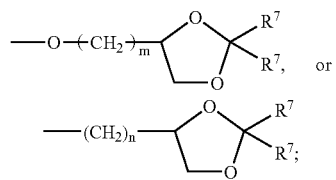

wherein when two $R^6$ are —$OR^{11}$ and are located adjacent to each other on a phenyl ring, the alkyl moieties of the two $R^6$ may be bonded together to form a methylenedioxy group;

each $R^7$ is, independently, hydrogen or lower alkyl;

each $R^8$ is, independently, hydrogen, lower alkyl, —C(=O)—$R^{11}$, glucuronide, 2-tetrahydropyranyl, or

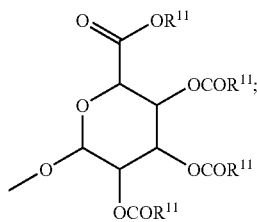

each $R^9$ is, independently, —$CO_2R^7$, —$CON(R^7)_2$, —$SO_2CH_3$, or —C(=O)$R^7$;

each $R^{10}$ is, independently, —H, —$SO_2CH_3$, —$CO_2R^7$, —C(=O)$NR^7R^9$, —C(=O)$R^7$, or —$CH_2$—(CHOH)$_n$—$CH_2OH$;

each Z is, independently, CHOH, C(=O), CHNR$^7R^{10}$, C=NR$^{10}$, or NR$^{10}$;

each $R^{11}$ is, independently, lower alkyl;

each g is, independently, an integer from 1 to 6;

each m is, independently, an integer from 1 to 7;

each n is, independently, an integer from 0 to 7;

each Q is, independently, C—$R^6$ or a nitrogen atom, wherein at most 3 Q in a ring are nitrogen atoms;

or a pharmaceutically acceptable salt thereof, and inclusive of all enantiomers, diastereomers, and racemic mixtures thereof.

The present also provides pharmaceutical compositions which contain a compound represented above.

The present invention also provides a method of promoting hydration of mucosal surfaces, comprising:

administering an effective amount of a compound represented by formula (I) to a mucosal surface of a subject.

The present invention also provides a method of restoring mucosal defense, comprising:

topically administering an effective amount of compound represented by formula (I) to a mucosal surface of a subject in need thereof.

The present invention also provides a method of blocking ENaC, comprising:

contacting sodium channels with an effective amount of a compound represented by formula (I).

The present invention also provides a method of promoting mucus clearance in mucosal surfaces, comprising:

administering an effective amount of a compound represented by formula (I) to a mucosal surface of a subject.

The present invention also provides a method of treating chronic bronchitis, comprising:

administering an effective amount of a compound represented by formula (I) to a subject in need thereof.

The present invention also provides a method of treating cystic fibrosis, comprising:

administering an effective amount of compound represented by formula (I) to a subject in need thereof.

The present invention also provides a method of treating rhinosinusitis, comprising:

administering an effective amount of a compound represented by a formula (I) to a subject in need thereof.

The present invention also provides a method of treating nasal dehydration, comprising:

administering an effective amount of a compound represented by formula (I) to the nasal passages of a subject in need thereof.

The present invention also provides a method of treating nasal dehydration, where the nasal dehydration is brought on by administering dry oxygen to the subject.

The present invention also provides a method of treating sinusitis, comprising:

administering an effective amount of a compound represented by formula (I) to a subject in need thereof.

The present invention also provides a method of treating pneumonia, comprising:

administering an effective amount of a compound represented by formula (I) to a subject in need thereof.

The present invention also provides a method of preventing ventilator-induced pneumonia, comprising:

administering an effective compound represented by formula (I) to a subject by means of a ventilator.

The present invention also provides a method of treating asthma, comprising:

administering an effective amount of a compound represented by formula (I) to a subject in need thereof.

The present invention also provides a method of treating primary ciliary dyskinesia, comprising:

administering an effective amount of a compound represented by formula (I) to a subject in need thereof.

The present invention also provides a method of treating otitis media, comprising:

administering an effective amount of a compound represented by formula (I) to a subject in need thereof.

The present invention also provides a method of inducing sputum for diagnostic purposes, comprising:

administering an effective amount of compound represented by formula (I) to a subject in need thereof.

The present invention also provides a method of treating chronic obstructive pulmonary disease, comprising:

administering an effective amount of a compound represented by formula (I) to a subject in need thereof.

The present invention also provides a method of treating emphysema, comprising:

administering an effective amount of a compound represented by formula (I) to a subject in need thereof.

The present invention also provides a method of treating dry eye, comprising:
administering an effective amount of a compound represented by formula (I) to the eye of the subject in need thereof.

The present invention also provides a method of promoting ocular hydration, comprising:
administering an effective amount of a compound represented by formula (I) to the eye of the subject.

The present invention also provides a method of promoting corneal hydration, comprising:
administering an effective amount of a compound represented by formula (I) to the eye of the subject.

The present invention also provides a method of treating Sjögren's disease, comprising:
administering an effective amount of compound represented by formula (I) to a subject in need thereof.

The present invention also provides a method of treating vaginal dryness, comprising:
administering an effective amount of a compound represented by formula (I) to the vaginal tract of a subject in need thereof.

The present invention also provides a method of treating dry skin, comprising:
administering an effective amount of a compound represented by formula (I) to the skin of a subject in need thereof.

The present invention also provides a method of treating dry mouth (xerostomia), comprising:
administering an effective amount of compound represented by formula (I) to the mouth of the subject in need thereof.

The present invention also provides a method of treating distal intestinal obstruction syndrome, comprising:
administering an effective amount of compound represented by formula (I) to a subject in need thereof.

The present invention also provides a method of treating esophagitis, comprising:
administering an effective amount of a compound represented by formula (I) to a subject in need thereof.

The present invention also provides a method of treating constipation, comprising:
administering an effective amount of a compound represented by formula (I) to a subject in need thereof. In one embodiment of this method, the compound is administered either orally or via a suppository or enema.

The present invention also provides a method of treating chronic diverticulitis comprising:
administering an effective amount of a compound represented by formula (I) to a subject in need thereof.

BRIEF DESCRIPTION OF THE FIGURES

A more complete appreciation of the invention and many of the attendant advantages thereof will be readily obtained as the same becomes better understood by reference to the following detailed description considered in conjunction with the following figures.

DETAILED DESCRIPTION OF THE INVENTION

Figure 1:
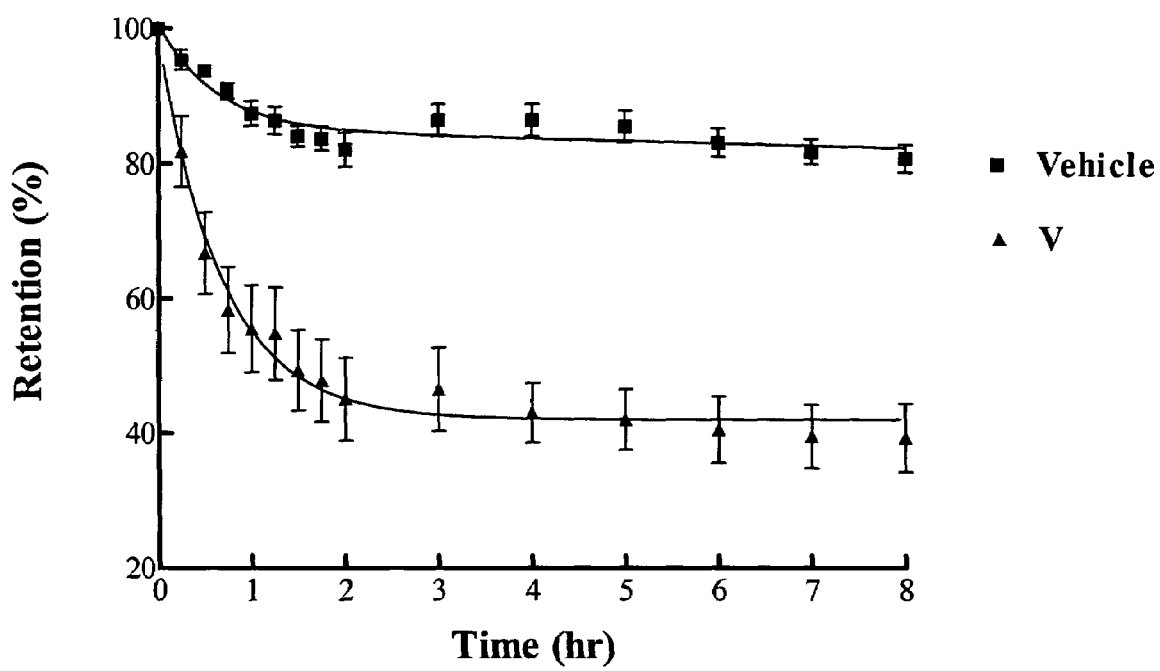
FIG. 1: Effect of a compound of the present invention on MCC at t=0 hrs as described in Example 9 herein.

The present invention is based on the discovery that the compounds of formula (I) are more potent and/or, absorbed less rapidly from mucosal surfaces, especially airway surfaces, and/or less reversable from interactions with ENaC as compared to compounds such as amiloride, benzamil, and phenamil. Therefore, the compounds of formula have a higher half-life on mucosal surfaces as compared to these compounds.

The present invention is also based on the discover that certain compounds embraced by formula (I) are converted in vivo into metabolic derivatives thereof which have reduced efficacy in blocking sodium channels as compared to the parent administered compound, after they are absorbed form mucosal surfaces after administration. This important property means that the compounds will have a lower tendency to cause undesired side-effects by blocking sodium channels located at untargeted locations in the body of the recipient, e.g., in the kidneys.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges therebetween, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Example of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or —N($R^2$)$_2$. The alkyl moiety of the lower alkoxy groups is the same as described above. Examples of mononuclear aryl include phenyl groups. The phenyl group may be unsubstituted or substituted as described above. The preferred identity of Y is —N($R^2$)$_2$. Particularly preferred are such compounds where each $R^2$ is hydrogen.

$R^1$ may be hydrogen or lower alkyl. Hydrogen is preferred for $R^1$.

Each $R^2$ may be, independently, —$R^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

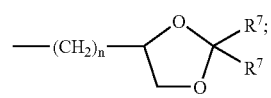

Hydrogen and lower alkyl, particularly $C_1$–$C_3$ alkyl are preferred for $R^2$. Hydrogen is particularly preferred.

$R^3$ and $R^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^3$ and $R^4$ is a group represented by formula (A).

Preferred compounds are those where one of $R^3$ and $R^4$ is hydrogen and the other is represented by formula (A).

In formula (A), the moiety $-(C(R^L)_2)_o\text{-x-}(C(R^L)_2)_p-$ defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, $C(=O)$, CHOH, $C(=N-R^{10})$, $CHNR^7R^{10}$, or represents a single bond;

Therefore, when x represents a single bond, the alkylene chain bonded to the ring is represented by the formula $-(C(R^L)_2)_{o+p}-$, in which the sum o+p is from 1 to 10.

Each $R^L$ may be, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, O-glucuronide, O-glucose, or

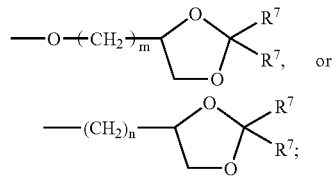

The preferred $R^L$ groups include $-H$, $-OH$, $-N(R^7)_2$, especially where each $R^7$ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula $-CHR^L-$. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula $-(CH_2)_o\text{-x-}(CH_2)_p-$.

There are four $R^6$ groups present on the ring in formula (A). Each $R^6$ may be each, independently, $-R^7$, $-OH$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, O-glucuronide, O-glucose,

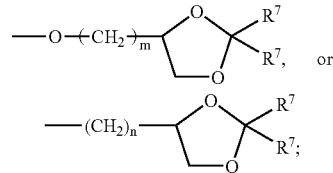

When two $R^6$ are $-OR^{11}$ and are located adjacent to each other on a phenyl ring, the alkyl moieties of the two $R^6$ groups may be bonded together to form a methylenedioxy group, i.e., a group of the formula $-O-CH_2-O-$.

As discussed above, $R^6$ may be hydrogen. Therefore, 1, 2, 3, or 4 $R^6$ groups may be other than hydrogen. Preferably at most 3 of the $R^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Q in formula (A) is $C-R^6$ or a nitrogen atom, where at most three Q in a ring are nitrogen atoms. Thus, there may be 1, 2, or 3 nitrogen atoms in a ring. Preferably, at most two Q are nitrogen atoms. More preferably, at most one Q is a nitrogen atom. In one particular embodiment, the nitrogen atom is at the 3-position of the ring. In another embodiment of the invention, each Q is $C-R^6$, i.e., there are no nitrogen atoms in the ring.

In a preferred embodiment of the present invention:

X is halogen;

Y is $-N(R^7)_2$;

$R^1$ is hydrogen or $C_1-C_3$ alkyl; $-(CH_2)_n-CO_2R^7$;

$R^2$ is $-R^7$, $-(CH_2)_m-OR^7$, or $-CO_2R^7$;

$R^3$ is a group represented by formula (A); and $R^4$ is hydrogen, a group represented by formula (A), or lower alkyl;

In another preferred embodiment of the present invention:

X is chloro or bromo;

Y is $-N(R^7)_2$;

$R^2$ is hydrogen or $C_1-C_3$ alkyl;

at most three $R^6$ are other than hydrogen as described above;

at most three $R^L$ are other than hydrogen as described above; and at most 2 Q are nitrogen atoms.

In another preferred embodiment of the present invention:

Y is $-NH_2$.

In another preferred embodiment of the present invention:

$R^4$ is hydrogen;

at most one $R^L$ is other than hydrogen as described above;

at most two $R^6$ are other than hydrogen as described above; and at most 1 Q is a nitrogen atom.

In another preferred embodiment of the present invention, x is O, NR⁷, C=O, CHOH, or C=N—R⁶. In another preferred embodiment of the present invention, x represents a single bond.

In another preferred embodiment of the present invention, each R⁶ is hydrogen. In another preferred embodiment of the present invention, at most two R⁶ are other than hydrogen as described above. In another preferred embodiment of the present invention, one R⁶ is other than hydrogen as described above. In another preferred embodiment of the present invention, one R⁶ is —OH.

In another preferred embodiment of the present invention, each $R^L$ is hydrogen. In another preferred embodiment of the present invention, at most two $R^L$ are other than hydrogen as described above. In another preferred embodiment of the present invention, one $R^L$ is other than hydrogen as described above.

In another preferred embodiment of the present invention, x represents a single bond and the sum of o and p is 4 to 6.

In another preferred embodiment of the present invention the compound of formula (I) is represented by the formula:

In another preferred embodiment of the present invention the compound of formula (I) is represented by the formula:

In another preferred embodiment of the present invention the compound of formula (I) is represented by the formula:

In another preferred embodiment of the present invention the compound of formula (I) is represented by the formula:

In another preferred embodiment of the present invention the compound of formula (I) is represented by the formula:

In another preferred embodiment of the present invention the compound of formula (I) is represented by the formula:

The compounds of formula (I) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formula (I) are embraced by the present invention. All mixtures of such enantiomers and diastereomers are within the scope of the present invention.

Without being limited to any particular theory, it is believed that the compounds of formula (I) function in vivo as sodium channel blockers. By blocking epithelial sodium channels present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., staphylococcus infections such as Staphylococcus aureus infections, Hemophilus influenza infections, Streptococcus pneumoniae infections, Pseudomonas aeuriginosa infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhinosinal surfaces by topical delivery, including aerosols and drops.

The present invention may be used to hydrate mucosal surfaces other than airway surfaces. Such other mucosal surfaces include gastrointestinal surfaces, oral surfaces, genito-urethral surfaces, ocular surfaces or surfaces of the eye, the inner ear and the middle ear. For example, the active compounds of the present invention may be administered by any suitable means, including locally/topically, orally, or rectally, in an effective amount.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9–10 of U.S. Pat. Nos. 6,264,975, 5,656,256, and 5,292,498, each of which is incorporated herein by reference.

Bronchdiloators can also be used in combination with compounds of the present invention. These Bronchodilators include, but are not limited to, $\beta$-adrenergic agonists including but not limited to epinephrine, isoproterenol, fenoterol, albuterol, terbutalin, pirbuterol, bitolterol, metaproterenol, iosetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genito-urethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10–500 μm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by an suitable means know in the art, such as by nose drops, mists., etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1, 1, 5 to about 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$–$10^4$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ Moles and more preferably from about $10^{-9}$ to about $10^{-4}$ Moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ Moles/liter, and more preferably from about $10^{-7}$ to about $10^{-4}$ Moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2–10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of pharmacy, chap. 86 (19$^{th}$ ed 1995). Pharmaceutical formulations suitable for nasal administration may be prepared as described in U.S. Pat. Nos. 4,389,393 to Schor; 5,707,644 to Illum; 4,294,829 to Suzuki; and 4,835,142 to Suzuki; the disclosures of which are incorporated by reference herein in the entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below.

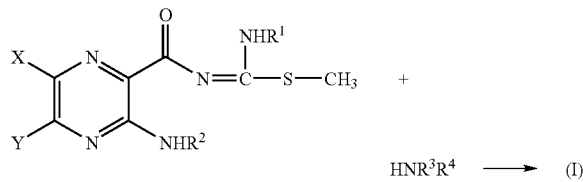

These procedures are described in, for example, E. J. Cragoe, "The Synthesis of Amiloride and Its Analogs" (Chapter 3) in *Amiloride and Its Analogs*, pp. 25–36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813.

Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1\times10^{-11}$ M to $3\times10^{-5}$M), and the cumulative change in $I_{SC}$ (inhibition) recorded. All drugs are prepared in dimethyl sulfoxide as stock solutions at a concentration of $1\times10^{-2}$ M and stored at $-20°$ C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls.

Pharmacological Assays of Absorption (1) Apical Disappearance Assay

Bronchial cells (dog, human, sheep, or rodent cells) are seeded at a density of $0.25\times10^{6}/cm^{2}$ on a porous Transwell-Col collagen-coated membrane with a growth area of 1.13 cm$^{2}$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_{t}$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 μl) and is initiated by adding experimental sodium channel blockers or positive controls (amiloride, benzamil, phenamil) to the apical surface at an initial concentration of 10 μM. A series of samples (5 μl volume per sample) is collected at various time points, including 0, 5, 20, 40, 90 and 240 minutes. Concentrations are determined by measuring intrinsic fluorescence of each sodium channel blocker using a Fluorocount Microplate Flourometer or HPLC. Quantitative analysis employs a standard curve generated from authentic reference standard materials of known concentration and purity. Data analysis of the rate of disappearance is performed using nonlinear regression, one phase exponential decay (Prism V 3.0).

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

3. In vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, we test for metabolism (generation of new species) using high performance liquid chromatography (HPLC) to resolve chemical species and the endogenous fluorescence properties of these compounds to estimate the relative quantities of test compound and novel metabolites. For a typical assay, a test solution (25 µl KBR, containing 10 µM test compound) is placed on the epithelial lumenal surface. Sequential 5 to 10 µl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolites, and HPLC mobilities of novel metabolites are then performed.

4. Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191–2196, incorporated herein by reference.

EXAMPLES

Having generally described this invention, a further understanding can be obtained by reference to certain specific examples which are provided herein for purposes of illustration only and are not intended to be limiting unless otherwise specified.

Materials and methods. All reagents and solvents were purchased from Aldrich Chemical Corp. and used without further purification. NMR spectra were obtained on either a Bruker WM 360 ($^1$H NMR at 360 MHZ and $^{13}$C NMR at 90 MHZ) or a Bruker AC 300 ($^1$H NMR at 300 MHZ and $^{13}$C NMR at 75 MHZ). Flash chromatography was performed on a Flash Elute™ system from Elution Solution (PO Box 5147, Charlottesville, Va. 22905) charged with a 90 g silica gel cartridge (40M FSO-0110–040155, 32–63 µm) at 20 psi ($N_2$). GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: $H_2$ at 40 ml/min., Air at 400 ml/min. Carrier gas: Split Ratio 16:1, $N_2$ flow at 15 ml/min., $N_2$ velocity at 18 cm/sec. The temperature program is 70° C. for 0–3 min, 70–300° C. from 3–10 min, 300° C. from 10–15 min.

HPLC analysis was performed on a Gilson 322 Pump, detector UV/Vis-156 at 360 mm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

4-(4-hydroxyphenyl)butylamidino-3,5-diamino-6-chloropyrazinecarboxamide hydrochloride (V)

The title compound was prepared as shown in Scheme 1 below. The 4-(4-hydroxyphenylbutyl)amine was prepared by routine organic transformations described in the following procedures. The coupling was done in accordance with the procedure described by Cragoe, E. J. Jr., Oltersdorf, O. W. Jr. and delSolms. S. J. (1981) U.S. Pat. No. 4,246,406, both incorporated herein by reference. The work up and purification were modified in accordance with the physical properties of V.

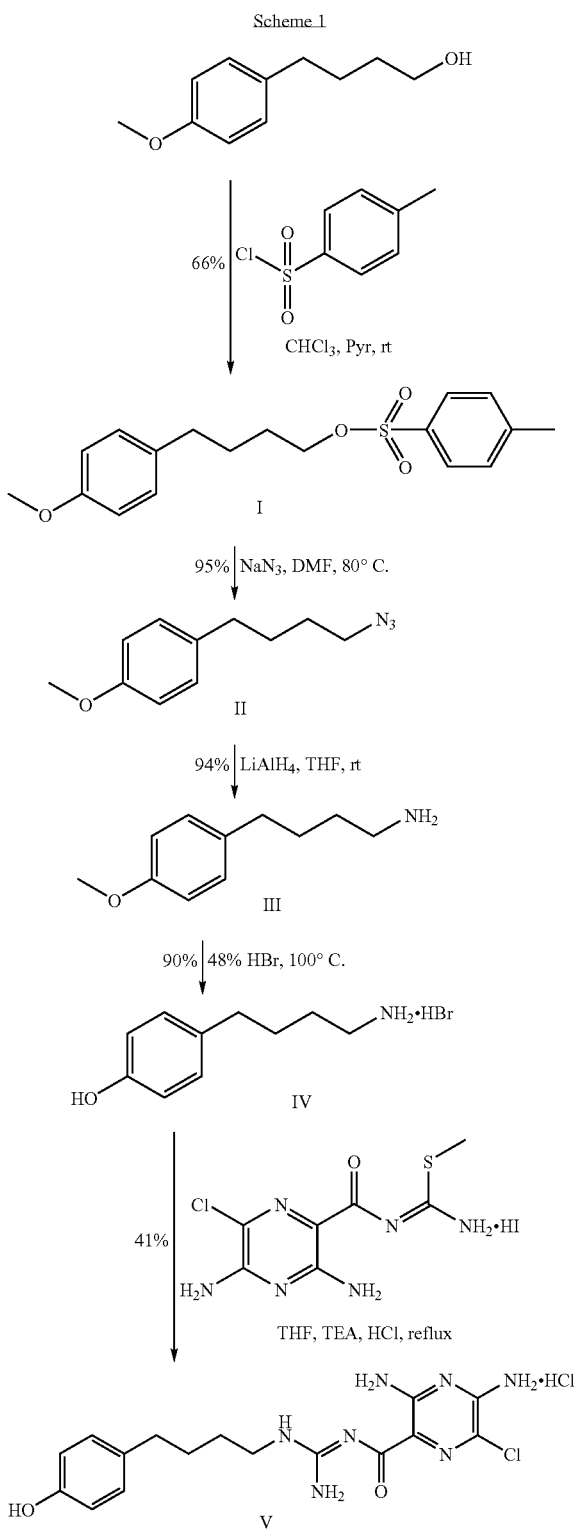

Scheme 1

4-Methylphenylsulfonic acid 4-(4-methoxyphenyl)butyl ester (I).

Pyridine (15 mL) was added dropwise to a cooled (0° C.) solution of 4-(4-methoxyphenyl)butanol (10.0 g, 0.055 mol) and p-toluenesulfonyl chloride (13.6 g, 0.072 mol) in dry chloroform (100 mL) under stirring. The reaction mixture was stirred overnight at room temperature. After this time, the reaction was quenched with 10% HCl (300 mL) and extracted with chloroform. The organic fraction was washed with saturated $NaHCO_3$, water and dried over magnesium sulfate. The solvent was removed under reduced pressure and the residue purified by flash chromatography (eluent: hexane, ethyl acetate=15:1) to provide 12.9 g (66%) of I as clear oil. $^1$H NMR (360 MHZ, $CDCl_3$) δ 1.61 (m, 4H), 2.44 (s, 3H), 2.52 (m, 2H), 3.78 (s, 3H), 4.05 (m, 2H), 6.77 (d, J=12.5 Hz, 2H), 7.05 (d, J=12.5 Hz, 2H), 7.34 (d, J=10.5 Hz, 2H), 7.78 (d, J=10.5 Hz, 2H).

4-(4-Methoxyphenyl)butylazide (II).

Sodium azide (3.07 g, 0.047 mol) was added to a solution of II (12.9 g, 0.04 mol) in anhydrous DMF (70 mL) and the reaction mixture was stirred 12 h at 80° C. (oil bath). Then solvent was removed at reduced pressure and the residual oil was treated with a mixture of $CH_2Cl_2$:ether=3:1 (100 mL). The resulting solution was washed with water (2×100 mL), brine and dried over magnesium sulfate. The solvent was removed under reduced pressure and 7.6 g (95%) of II was obtained. The purity of II (99%) was determined by GC and TLC (eluent:hexane, ethyl acetate=1:1), $R_f$=0.84.

4-(4-Methoxyphenyl)butylamine (III).

Lithium aluminum hydride (55 mL of a 1M solution in THF, 0.055 mol) was added drop wise to a solution of II (7.6 g, 0.037 mol) in dry THF (70 mL) at 0° C. and stirred overnight at room temperature in an argon atmosphere. The reaction mixture was treated with water (1.5 mL), then 15% NaOH (1.5 mL), then with more water (3 mL) and filtered. The solid precipitate was washed with THF. The combined organic fractions were dried over magnesium sulfate and the solvent was removed under reduced pressure to give 6.2 g (94%) of III. The purity of III (99%) was determined by GC. $^1$H NMR (360 MHz, DMSO-$d_6$) δ 1.34 (m, 2H), 1.54 (m, 2H), 2.51 (m, 4H), 3.70 (s, 3H), 6.83 (d, J=8.6 Hz, 2H), 7.08 (d, J=8.3 Hz, 2H); $^{13}$C(90 MHz, DMSO-$d_6$) δ 28.6, 330, 34.1, 41.5, 54.8, 113.1, 129.1, 132.2, 157.3

4-(4-Hydroxyphenyl)butylamine hydrobromide (IV).

Amine III (2.32 g, 0.012 mol) was stirred in boiling 48% HBr (50 mL) for 3 h. After the reaction was completed, argon was bubbled through the solution and the solvent was evaporated under reduced pressure. The solid residue was dried above KOH to provide 3.1 g (90%) of IV. API MS m/z=166[$C_{10}H_{15}NO+H$]$^+$

4-(4-Hydroxyphenyl)butylamidino-3,5-diamino-6-chloro-pyrazinecarboxamide hydrochloride (V).

1-(3,5-Diamino-6-chloropyrazinoyl-2-methyl-pseudothiourea hydroiodide (0.4 g, 1.03 mmol) was added to a suspension of 4-(4-hydroxyphenyl)butylamine hydrobromide (IV) in a mixture of THF (35 mL) and triethylamine (3 mL). The reaction mixture was stirred at reflux temperature for 3 h, then the supernatant was separated and the solvent was removed under reduced pressure. The oily residue was washed with water (2×30 mL), ether (3×30 mL) and then 10% HCl (40 mL) was added. The mixture was vigorously stirred for 10 min then the yellow solid was filtered off, dried and recrystallized twice from ethanol to give 181 mg (41%) of V as yellow solid. Purity is 98% by HPLC, retention time is 9.77 min; $^1$H NMR (300 MHz, DMSO-$d_6$) δ 1.56 (br s, 4H), 2.48 (br s, 2H), 3.35 (m, 2H), 6.65 (d, J=8.5 Hz, 2H), 6.95 (d, J=8.6 Hz, 2H), 7.50 (br s, 2H), 8.75 (br s, 1H), 9.05 (br .s, 1H), 9.33 (br s, 2H), 10.55 (s, 1H); $^{13}$C NMR (75 MHz, $CD_3OD$) 28.7, 29.8, 35.4, 42.4, 111.2, 116.1, 122.0, 130.0, 134.0, 155.0, 156.1, 156.8, 157.5, 167.0; APCI MS m/z=378 $[C_{16}H_{20}ClN_7O_2+H]^+$.

Example 2

4-(4-Hydroxyphenyl)butylamidino-3,5-diamino-6-chloropyrazinecarboxamide hydrochloride

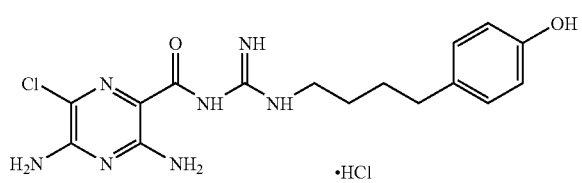

4-Methylphenylsulfonic acid 4-(4-methoxyphenyl)butyl ester (1).

Pyridine (15 mL) was added drop wise to a cooled (0° C.) solution of 4-(4-methoxyphenyl)butanol (10.0 g, 0.055 mol) and p-toluenesulfonyl chloride (13.6 g, 0.072 mol) in dry chloroform (100 mL) under stirring. The reaction mixture was stirred overnight at room temperature. After this time, the reaction was quenched with 10% HCl (300 mL) and extracted with chloroform. The organic fraction was washed with saturated $NaHCO_3$, water and dried over magnesium sulfate. The solvent was removed under reduced pressure and the residue purified by flash chromatography (eluent: hexane/ethyl acetate 15:1) to provide 12.9 g (66%) of 1 as clear oil. $^1$H NMR (360 MHz, $CDCl_3$) δ 1.61 (m, 4H), 2.44 (s, 3H), 2.52 (m, 2H), 3.78 (s, 3H), 4.05 (m, 2H), 6.77 (d, 2H), 7.05 (d, 2H), 7.34 (d, 2H), 7.78 (d, 2H).

4-(4-Methoxyphenyl)butylazide (2).

Sodium azide (3.07 g, 0.047 mol) was added to a solution of 1 (12.9 g, 0.04 mol) in anhydrous DMF (70 mL) and the reaction mixture was stirred 12 h at 80° C. (oil bath). Then solvent was removed at reduced pressure and the residual oil was treated with a mixture of $CH_2Cl_2$/ether 3:1 (100 mL). The resulting solution was washed with water (2×100 mL), brine and dried over magnesium sulfate. The solvent was removed under reduced pressure and 7.6 g (95%) of 2 was obtained. The purity of 2 (99%) was determined by GC and TLC (eluent:hexane/ethyl acetate 1:1), $R_f$=0.84.

4-(4-Methoxyphenyl)butylamine (3). Typical Procedure A

Lithium aluminum hydride (LAH) (55 mL of a 1.0 M solution in THF, 0.055 mol) was added drop wise to a solution of 2 (7.6 g, 0.037 mol) in dry THF (70 mL) at 0° C. The mixture was stirred overnight at room temperature in an argon atmosphere then the mixture was treated with water (1.5 mL), then 15% NaOH (1.5 mL), then with more water (3 mL) and filtered. The solid precipitate was washed with THF. The combined organic fractions were dried over magnesium sulfate and the solvent was removed under reduced pressure to give 6.2 g (94%) of 3. The purity of 3 (99%) was determined by GC. $^1$H NMR (360 MHz, DMSO-$d_6$) δ 1.34 (m, 2H), 1.54 (m, 2H), 2.51 (m, 4H), 3.70 (s, 3H), 6.83 (d, 2H), 7.08 (d, 2H). $^{13}$C NMR (90 MHz, DMSO-$d_6$) δ 28.6, 330, 34.1, 41.5, 54.8, 113.1, 129.1, 132.2, 157.3

4-(4-Hydroxyphenyl)butylamine hydrobromide (4). Typical Procedure B Amine 3 (2.32 g, 0.012 mol) was stirred in boiling 48% HBr (50 mL) for 3 h. After the reaction was completed, argon was bubbled through the solution and the solvent was evaporated under reduced pressure. The solid residue was dried above KOH to provide 3.1 g (90%) of 4. APCI MS m/z=166$[C_{10}H_{15}NO+H]^+$.

4-(4-Hydroxyphenyl)butylamidino-3,5-diamino-6-chloropyrazinecarboxamide hydrochloride (5).

1-(3,5-Diamino-6-chloropyrazinoyl-2-methyl-pseudothiourea hydroiodide (0.4 g, 1.03 mmol) was added to a suspension of 4-(4-hydroxyphenyl)butylamine hydrobromide (4) (0.8 g, 32 mmol) in a mixture of THF (35 mL) and triethylamine (3 mL). The reaction mixture was stirred in the boiling solvent for 3 h, then the supernatant was separated and the solvent was removed under reduced pressure. The oily residue was washed with water (2×30 mL), ether (3×30 mL) and then 10% HCl (40 mL) was added. The mixture was vigorously stirred for 10 min then the yellow solid was filtered off, dried and recrystallized twice from ethanol to give 5 (0.18 g, 41%) as yellow solid. Purity is 98% by HPLC, retention time is 9.77 min. $^1$H NMR (300 MHz, DMSO-$d_6$) δ 1.56 (br s, 4H), 2.48 (br s, 2H), 3.35 (m, 2H), 6.65 (d, 2H), 6.95 (d, 2H), 7.50 (br s, 2H), 8.75 (br s, 1H), 9.05 (br s, 1H), 9.33 (br s, 2H), 10.55 (s, 1H). $^{13}$C NMR (75 MHz, $CD_3OD$) 28.7, 29.8, 35.4, 42.4, 111.2, 116.1, 122.0, 130.0, 134.0, 155.0, 156.1, 156.8, 157.5, 167.0. APCI MS m/z=378 $[C_{16}H_{20}ClN_7O_2+H]^+$.

Example 3

3-(4-Hydroxyphenyl)propylamidino-3,5-diamino-6-chloropyrazinecarboxamide hydrochloride

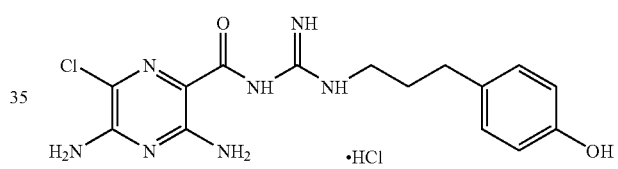

Methanesulfonic acid 3-(4-methoxyphenyl)propyl ester (11). Typical Procedure E.

Pyridine (15 mL) was added drop wise to a cooled (0° C.) solution of 4-(4-methoxyphenyl)propanol (10.0 g, 0.06 mol) and methanesulfonyl chloride (14.7 g, 0.078 mol) in dry THF (70 mL) under stirring. The reaction mixture was stirred overnight at room temperature. After this time, the solvent was removed under reduced pressure and the residue was quenched with 10% HCl (300 mL) and extracted with ethyl acetate. The organic fraction was washed with saturated $NaHCO_3$, water and dried over sodium sulfate. The solvent was removed and the residual crude ester 11 was used in the next step without further purification. Compound 11 was obtained as a yellow oil (8.8 g, 60%). $^1$H NMR (300 MHz, $CDCl_3$) δ 2.08 (m, 2H), 2.60 (m, 2H), 2.98 (m, 2H) 3.98 (s, 3H), 3.66 (s, 3H), 6.85 (d, 2H), 7.03 (d, 2H).

3-(4-Methoxyphenyl)propylazide (12).

Azide 12 was prepared according to procedure C from 11 (8.8 g, 0.036 mol) and sodium azide (3 g, 0.045 mol) in 75% yield. $^1$H NMR (300 MHz, $CDCl_3$) δ 1.90 (m, 2H), 2.65 (t, 2H), 3.28 (m, 2H), 3.80 (s, 3H), 6.85 (d, 2H), 7.10 (d, 2H).

3-(4-Methoxyphenyl)propylamine (13).

Amine 13 was prepared as described in procedure A from azide 12 (5.2 g, 0.027 mol) and LAH (26 ml of 1 M solution in THF).

Crude 13 was purified by flash chromatography (silica gel, 2:1:0.05 chloroform/ethanol/concentrated ammonium hydroxide) to provide pure amine 13 (3.2 g, 74%) as a clear oil. $^1$H NMR (300 MHz, CDCl$_3$) δ 1.58 (m, 2H), 2.50 (m, 4H), 3.72 (s, 3H), 6.85 (d, 2H), 7.10 (d, 2H).

3-(4-Hydroxyphenyl)propylamine hydrobromide (14).

Compound 14 was synthesized according to procedure B from 13 (2.5 g, 0.015 mol) in 75% yield as a light brown solid. $^1$H NMR (300 MHz, DMSO-d$_6$) δ 1.80 (m, 2H), 2.53 (m, 2H), 2.78 (m, 2H), 6.70 (d, 2H), 7.02 (d, 2H), 7.80 (br s, 4H).

3-(4-Hydroxyphenyl)propylamidino-3,5-diamino-6-chloropyrazinecarboxamide hydrochloride (15).

Triethylamine (8 mL) was added to suspension of compound 14 (0.470 g, 2 mmol) in THF (40 mL) and the mixture was stirred at room temperature for 15 min. After this time 1-(3,5-diamino-6-chloropyrazinoyl-2-methyl-pseudothiourea hydroiodide (0.15 g, 0.4 mmol) was added and the mixture was stirred at reflux for 3 h. The solution was then cooled to room temperature and the supernatant was isolated. The solvent was evaporated and the residual oil was washed with ether (2×50 mL), ethyl acetate (50 mL) and treated with 20 ml of 10% HCl. The obtained solid was isolated by filtration and dissolved in MeOH (approx. 50 mL). Addition of ethyl acetate (20 mL) to the solution caused the precipitation of a yellow solid, which was isolated by centrifugation, washed with ethyl acetate and dried under vacuum to give compound 15 (48 mg, 31%) as a yellow solid. $^1$H NMR (300 MHz, DMSO-d$_6$) δ 1.80 (br s, 2H), 2.58 (m, 2H), 3.95 (br s, 4H), 6.70 (d, 2H), 7.03 (d, 2H), 7.48 (br. s, 2H), 8.80 (br s, 1H), 8.93 (br s, 1H), 9.32 (br s, 2H), 10.52 (s, 1H). APCI MS m/z=364 [C$_{15}$H$_{18}$ClN$_7$O$_2$+H]$^+$.

Example 4

5-(4-Hydroxyphenyl)pentylamidino-3,5-diamino-6-chloropyrazinecarboxamide hydrochloride

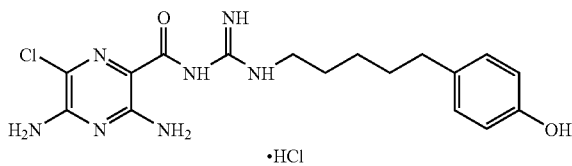

•HCl 5-(4-Methoxyphenyl)pent-4-yn-1-ol (16).

4-Iodoanisol (10 g, 42 mmol), palladium (II) chloride (0.2 g, 1.1 mmol) and triphenylphosphine (0.6 g, 2.2 mmol) were dissolved in diethylamine (100 mL) then cupper(I) iodide (0.5 g, 2.2 mmol) and 4-pentyn-1-ol (5 mL, 53 mmol) were added. The reaction mixture was stirred overnight at room temperature, then the solvent was removed under reduced pressure. Ethyl acetate (150 mL) was added to the residue and the mixture was washed with 2N HCl, brine and water. The organic fraction was isolated, dried with sodium sulfate and the solvent was removed under reduced pressure. The product 16 (7.1 g. 87%) was isolated by flash chromatography (silica gel, 1:2 ethyl acetate/hexanes) as an oily yellow solid. $^1$H NMR (300 MHz, CDCl$_3$) δ 1.88 (m, 2H), 2.53 (m, 2H), 3.72 (s, 3H), 3.74 (m, 2H), 6.83 (d, 2H), 7.45 (d, 2H).

5-(4-Methoxyphenyl)pentane-1-ol (17).

A solution of 16 (7.1 g, 37 mmol) in 150 dry ethanol (150 mL) was placed in a 0.5 L Parr flask and palladium on carbon (0.92 g, 5% wet. Pd/C) was added as a suspension in ethanol (25 mL). The reaction mixture was shaken at 50 psi of hydrogen pressure at room temperature for 24 hours. After this time, the mixture was filtered through a silica gel pad and the solvent was removed at reduced pressure. The residue was purified by flash chromatography (silica gel, 1:3 ethyl acetate/hexanes) to provide 17 (6.7 g, 92%) as a clear oil. $^1$H NMR (300 MHz, CDCl$_3$) δ 1.48 (m, 2H), 1.60 (m, 4H), 2.58 (m, 2H), 3.63 (m, 2H) 3.80 (s, 3H), 6.83 (d, 2H), 7.10 (d, 2H).

Methanesulfonic acid 4-(4-methoxyphenyl)pentyl ester (18).

Ester 18 was prepared following procedure E from alcohol 17 (6.7 g, 34.5 mmol) and methanesulfonyl chloride (4.5 mL, 50 mmol). The crude product 18 (9.0 g) was obtained as a brown oil and used in the next step without purification.

5-(4-Methoxyphenyl)pentyl azide (19).

Compound 19 was synthesized according to procedure C from crude 18 (9.0 g) and sodium azide (2.7 g, 40 mmol). Azide 19 (6 g, 79% from 17) was isolated by flash chromatography (silica gel, 1:1 ethyl acetate/hexanes). $^1$H NMR (300 MHz, CDCl$_3$) δ 1.40 (m, 2H), 1.62 (m, 4H), 2.56 (m, 2H), 3.35 (m, 2H) 3.80 (s, 3H), 6.85 (d, 2H), 7.10 (d, 2H).

5-(4-Methoxyphenyl)pentyl amine (20).

Amine 20 was made following procedure A from 19 (6 g, 27 mmol) and LAH (26 mL of 1.0M solution in THF) in 70% yield. $^1$H NMR (300 MHz, CDCl$_3$) δ 1.35(m, 2H), 1.48 (m, 2H) 1.61 (m, 2H), 2.55 (m, 2H), 2.70 (m, 2H) 3.80 (s, 3H), 6.85 (d, 2H), 7.10 (d, 2H).

5-(4-Hydroxyphenyl)pentyl amine (21).

The HBr salt of 21 was prepared according to procedure B from amine 20 (2.8 g, 14 mmol). Free amine 21 (2 g, 80%) was obtained after flash chromatography (silica gel, 6:3:0.1, chloroform/ethanol/concentrated ammonium hydroxide) as a cloudy oil. $^1$H NMR (300 MHz, DMSO-d$_6$) δ 1.28(m, 2H), 1.55 (m, 2H), 1.61 (m, 2H), 2.48 (m, 2H), 2.58 (m, 2H), 6.68 (d, 2H), 6.98 (d, 2H).

5-(4-Hydroxyphenyl)pentylamidino-3,5-diamino-6-chloropyrazinecarboxamide hydrochloride (22).

1-(3,5-Diamino-6-chloropyrazinoyl-2-methyl-pseudothiourea hydroiodide (0.25 g, 0.65 mmol) was added to a solution of 21 (0.6 g, 3.4 mmol) in THF (50 mL). The reaction mixture was stirred at reflux for 2 h, then the solvent was removed under reduced pressure and the resulting oil was washed with ether (2×50 mL) and treated with ethyl acetate until a yellow powder was formed. The yellow solid was dissolved in methanol (70 mL) and the volume was slowly reduced until precipitation began (approximately 25 mL). The solution was cooled to 0° C. and the precipitate was collected by centrifugation. Diluted HCl (20 mL of a 10% solution) was added and the mixture was vigorously stirred for 20 min, then the precipitate was filtered off, washed with cold water, and dried to give 22 (183 mg, 39%) as a yellow solid. $^1$H NMR (300 MHz, DMSO-d$_6$) δ 1.32 (br s, 2H), 1.55 (m, 4H), 2.45 (m, 2H), 3.29 (m, 2H), 6.68 (d, 2H), 6.97 (d, 2H), 7.46 (s, 1H), 8.00 (br s, 1H), 8.83 (br s, 1H), 8.97 (br s, 1H), 9.46 (d, 2H), 10.55 (s, 1H). APCI MS m/z=392[C$_{17}$H$_{22}$ClN$_7$O$_2$+H]$^+$.

Example 5

4-(3,4-Dihydroxyphenyl)butylamidino-3,5-diamino-6-chloropyrazinecarboxamide hydrochloride

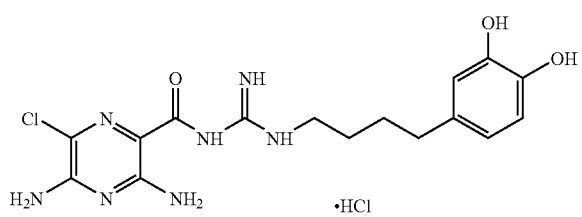

4-(3,4-Dimethoxyphenyl)butanol (23).

4-(3,4-Dimethoxyphenyl)butyric acid (13 g, 58 mmol) was dissolved in dry THF (150 mL) then $BH_3$.THF (110 mL, 1M solution, 110 mmol) was added drop wise with vigorous stirring under an argon atmosphere. The reaction mixture was then stirred overnight at room temperature. After this time, the reaction was quenched with water and 10% HCl solution at 0° C. and extracted with ethyl acetate. The organic fraction was dried with sodium sulfate and passed through a pad of silica gel. The solvent was removed at reduced pressure to give 23 (12.0 g, 99%) as a clear oil. $^1$H NMR (300 MHz, $CDCl_3$) δ 1.62 (m, 4H), 2.0 (s, 1H), 2.62 (m, 2H), 3.65 (m, 2H), 3.82 (s, 3H), 3.84 (s, 3H) 6.67–6.82 (m, 3H).

Methanesulfonic Acid 4-(3,4-dimethoxyphenyl)butyl ester (24).

Ester 24 was prepared following procedure E from alcohol 23 (12.0 g, 57 mmol) and methanesulfonyl chloride (8.4 g, 74 mmol) in 78% yield. $^1$H NMR (300 MHz, $CDCl_3$) δ 1.65 (m, 4H), 2.62 (m, 2H), 3.05 (s, 3H), 3.88 (br s, 6H), 4.38 (m, 2H) 6.70–6.88 (m, 3H).

4-(3,4-Dimethoxyphenyl)butyl azide (25).

Compound 25 was synthesized according to procedure C from 24 (14.1 g 51 mmol) and sodium azide (4.0 g, 66 mmol) in 96% yield. $^1$H NMR (300 MHz, $CDCl_3$) δ 1.65 (m, 4H), 2.60 (m, 2H), 3.30 (m, 2H), 3.86 (br s, 6H), 6.70 (m, 2H), 6.78 (m, 1H).

4-(3,4-Dimetoxyphenyl)butyl amine (26).

Amine 26 was prepared as described in procedure A from azide 25 (11.0 g, 49 mol) and LAH (26 mL of 1 M solution in THF). Crude 26 was purified by flash chromatography (silica gel, 93:7:1 chloroform/ethanol/concentrated ammonium hydroxide) to give pure 26 (4.8 g, 42%) as a clear oil. $^1$H NMR (300 MHz, $CDCl_3$) δ 1.42(m, 2H), 1.60 (m, 2H), 2.55 (m, 2H), 2.74 (m, 2H), 3.82 (s, 6H), 3.84 (s, 3H), 6.70 (m, 2H), 6.78 (m, 1H).

4-(3,4-Dihydroxyphenyl)butyl amine hydrobromide (27).

Compound 27 was synthesized according to procedure B from 26 (2.5 g, 11 mmol) in 62% yield as a pink solid. $^1$H NMR (300 MHz, DMSO-$d_6$) δ 1.52 (br s, 4H), 2.40 (m, 2H), 2.78 (m, 2H), 6.42 (m, 1H), 6.60 (m, 2H), 7.80 (br s, 4H).

4-(3,4-Dihydroxyphenyl)butylamidino-3,5-diamino-6-chloropyrazinecarboxamide hydrochloride (28).

1-(3,5-Diamino-6-chloropyrazinoyl-2-methyl-pseudothiourea hydroiodide (0.2 g, 0.51 mmol) was added to a suspension of 27 in a mixture of THF (35 mL) and triethylamine (3 mL). The reaction mixture was stirred at reflux for 3 h, then the supernatant was separated and the solvent was removed under reduced pressure. The brown residue was washed with ether (2×30 mL) followed by addition of 10% HCl (5 mL). The solid material was collected, dissolved in methanol and precipitated by addition of ethyl acetate. The precipitate was washed with 10% HCl and dried to give compound 28 (131 mg, 51%) as a beige solid. $^1$H NMR (300 MHz, DMSO-$d_6$) δ 1.52 (br s, 4H), 2.42 (m, 2H), 3.31 (m, 2H), 6.43 (m, 1H), 6.61 (m, 2H), 7.42 (br s, 2H), 7.90 (br s, 1H), 8.82 (br s, 1H), 8.98 (br s, 1H), 9.25 (s, 1H) 10.52 (s, 1H). APCI MS m/z=394 $[C_{16}H_{20}ClN_7O_3+H]^+$.

Example 6

4-(4-Hydroxyphenyl)-4-oxabutylamidino-3,5-diamino-6-chloropyrazinecarboxamide hydrobromide

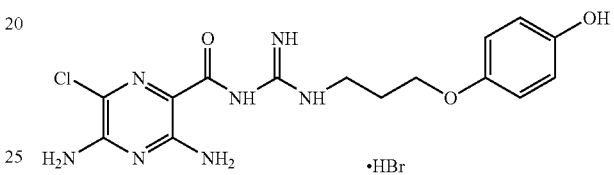

4-(4-Hydroxyphenyl)-4-oxabutylamidino-3,5-diamino-6-chloropyrazine carboxamide hydrobromide (63).

The vigorously stirred solution of 62 (80 mg, 0.19 mmol) in 48% HBr (15 mL) was refluxed 2 h and then cooled. The precipitate that formed was separated, washed with water and dried overnight to provide 63 (52 mg, 52%). $^1$H NMR (300 MHz, DMSO-$d_6$) δ 1.99 (m, 2H), 3.96 (m, 2H), 6.77 (m, 2H), 6.79 (m, 2H), 7.45 (s, 2H), 8.74 (br s, 1H), 8.87 (br s, 1H), 9.30 (s, 1H) 10.48 (s, 1H). APCI MS m/z 380 $[C_{15}H_{18}ClN_7O_3+H]^+$.

Example 7

4-(2,4-Dihydroxyphenyl)butylamidino-3,5-diamino-6-chloropyrazinecarboxamide hydrochloride

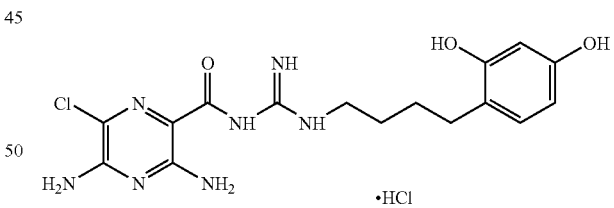

4-(2,4-Dimethoxyphenyl)-but-3-yn-1-ol (75).

1-Bromo-2,4-dimethoxybenzene (10 g 0.046 mol), palladium chloride (0.2 g 0.11 mmol) and triphenylphosphine (0.6 g 0.0023 mol) were dissolved in diethylamine (100 mL) under a nitrogen atmosphere. Copper (I) iodide (0.44 g 0.0023 mol) and 3-butyn-1-ol (7 mL 0.092 mol) were added into the reaction mixture at once. The mixture was stirred overnight at 55° C. under a nitrogen atmosphere. The catalyst was filtered off from the reaction mixture and the same amount of palladium chloride, triphenylphosphine, copper (I) iodide and 3-butyn-1-ol were added. The reaction mixture was stirred and heated at 85° C. for 48 hours. Then the solvent was removed at reduced pressure and water (approx. 100 mL) was added to the residue. The mixture was extracted with ethyl acetate (350 mL) passed through a pad of silica gel and concentrated. The product was purified by flash chromatography (silica gel, 1:1 hexanes/ethyl acetate). Compound 75 (4.2 g, 24%) was isolated as a brown oil. $^1$H NMR (300 MHz, CDCl$_3$) δ 2.24 (t, 1H), 2.73 (t, 2H), 3.80 (br s, 5H), 3.87 (s, 3H), 6.43 (m, 2H), 7.30 (m, 1 H).

4-(2,4-Dimethoxyphenyl)-butan-1-ol (76).

To a solution of 75 (4.2 g, 0.022 mol) in ethanol (approx. 200 mL) was added palladium (5% wet on activated carbon, 1 g). Then the mixture was hydrogenated at 40 psi overnight at room temperature. The mixture was filtered through a pad of silica gel and the solvent was evaporated to give 76 (4.15 g, 97%) as a yellow oil. $^1$H NMR (300 MHz, CDCl$_3$) δ 1.59 (m, 4H), 2.55 (m, 2H), 3.79 (s, 6H), 6.43 (m, 2H), 7.00 (m, 1H).

Methanesulfonic acid 4-(2,4-dimethoxyphenyl)butyl ester (77).

Ester 77 was prepared by typical procedure E from alcohol 76 (4.15 g, 0.021 mol), methanesulfonyl chloride (2.4 mL, 0.03 mol) and triethylamine (20 mL). Crude 77 (4.6 g, 80%) was isolated as a yellow oil 4-(2,4-Dimethoxyphenyl)butyl azide (78).

Azide 78 was prepared by typical procedure C from ester 77 (4.6 g, 0.015 mol) and sodium azide (1.5 g, 0.023 mol). Compound 77 (4.06 g, 75%) was isolated as a yellow oil. $^1$H NMR (300 MHz, CDCl$_3$) δ 1.62 (m, 4H), 2.58 (m, 2H), 3.30 (m, 2H), 3.80 (s, 6H), 6.43 (m, 2H), 7.00 (m, 1H).

4-(2,4-Dimethoxyphenyl)butyl amine (79).

Amine 79 was prepared by typical procedure A from azide 78 (4.06 g, 0.017 mol) and LiAlH$_4$ (13 mL of a 1.0 M solution in THF). The material was purified by column chromatography (silica gel, 2:1:0.1 chloroform/ethanol/concentrated ammonium hydroxide) to provide 79 (2.3 g, 64%) as a white solid. $^1$H NMR (300 MHz, CDCl$_3$) δ 1.53 (m, 4H), 2.53 (m, 2H), 2.73 (m, 2H), 3.80 (s, 6H), 6.43 (m, 2H), 7.52 (m, 1H).

4-(2,4-Dimethoxyphenyl)butylamidino-3,5-diamino-6-chloropyrazine carboxamide hydrochloride (80).

1-(3,5-Diamino-6-chloropyrazinoyl-2-methyl-pseudothiourea hydroiodide (0.3 g, 0.77 mmol) was added to an anhydrous THF solution (30 mL) of 79 (0.4 g, 1.9 mmol). The reaction mixture was stirred at reflux for 3 h then the solvent was evaporated. The residue was washed with ethyl acetate (2×20 mL) then treated with 3% HCl (15 mL). The yellow solid that formed was separated, washed with water and dried overnight to provide compound 80 (0.32 g, 90%). $^1$H NMR (300 MHz, DMSO-d$_6$) δ 1.57 (s, 4H), 2.50 (br s, 2H), 3.35 (br s, 2H), 3.73 (s, 3H), 3.76 (s, 3H), 6.43 (m, 1H), 6.52 (s, 1H), 7.02 (m, 1H), 7.45 (br s, 2H), 8.86 (br s, 1H), 8.99 (br s, 1H), 9.03 (m, 1H), 10.56 (s, 1H). APCI MS m/z 422 [C$_{18}$H$_{24}$ClN$_7$O$_3$+H]$^+$.

4-(2,4-Dihydroxyphenyl)butylamidino-3,5-diamino-6-chloropyrazine carboxamide hydrochloride (81).

A vigorously stirred solution of 80 (290 mg, 0.63 mmol) in 48% HBr (20 mL) was refluxed for 4 h and then cooled. The solvent was removed at reduced pressure and the material was purified by column chromatography (silica gel, 4:1:0.1 chloroform/ethanol/concentrated ammonium hydroxide). The fractions with product were collected and the solvent was removed under reduced pressure. The residue was treated with 3% HCl, washed with water (2×5 mL) and dried to provide 81 (79 mg, 32%) as a yellow solid. $^1$H NMR (300 MHz, DMSO-d$_6$) δ 1.54 (s, 4H), 2.43 (br s, 2H), 3.31 (br s, 2H), 6.12 (d, 1H), 6.32 (s, 1H), 6.78 (d, 1H), 8.86 (br s, 1H), 8.99 (br s, 1H), 9.28 (s, 1H), 10.56 (s, 1H). APCI MS m/z 394 [C$_{16}$H$_{20}$ClN$_7$O$_3$+H]$^+$.

REFERENCES

1. Taylor, E. C.; Harrington, P. M.; Schin,C. Heterocycles, 1989, 28, 1169
2. Widsheis et al, Synthesis, 1994, 87–92

Example 8

Sodium Channel Blocking Activity

The compounds shown in Tables 1–5 below were tested for potency in canine bronchial epithelia using the in vitro assay described above. Amiloride was also tested in this assay as a positive control. The results for the compounds of the present invention are reported as fold-enhancement values relative to amiloride.

TABLE 1

| Position | R | Fold Enhancement Over Amiloride |
|---|---|---|
| 2,4 | H | 14.9 |
| 3,5 | H | 13.7 |
| 3,4 | H | 15.1 |
| 2,5 | H | 20.3 |

TABLE 2

| n | Position of R | R | Fold Enhancement Over Amiloride |
|---|---|---|---|
| 5 | 4 | OH | 14 |
| 3 | 4 | OH | 5.2 |
| 4 | 4 | OH | 50.3 |

TABLE 3

| Q | R | Fold Enhancement Over Amiloride |
|---|---|---|
| N | OH | 9.5 |
| CH | OH | 50.3 |

TABLE 4

Cl—[pyrazine ring with NH₂, N, N, NH₂]—C(=O)—N=C(NH₂)—NH—CH₂CH₂—a—b—[phenyl]—OR

| a | b | R | Fold Enhancement Over Amiloride |
|---|---|---|---|
| $CH_2$ | O | H | 16.1 |

Example 9

Figure 2:
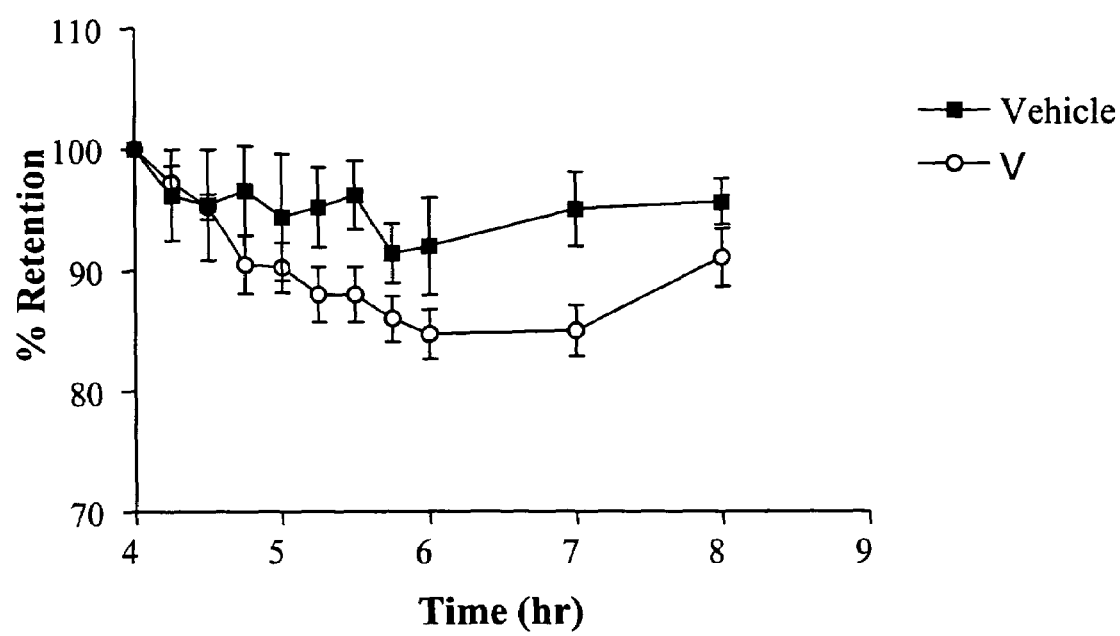
FIG. 2: Effect of a compound of the present invention on MCC at t=4 hrs as described in Example 9 herein.

Effect of 4-(4-hydroxyphenyl)butylamidino-3,5-diamino-6-chloropyrazinecarboxamide hydrochloride (V) on MCC This experiment was conducted with 4-(4-hydroxyphenyl)butylamidino-3,5-diamino-6-chloropyrazinecarboxamide hydrochloride (V), and the vehicle as a control. The results are shown in FIGS. 1 and 2.

Methods

Animal Preparation: The Mount Sinai Animal Research Committee approved all procedures for the in vivo assessment of mucociliary clearance. Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 μm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed radio-labeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration.

Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess over effects), followed by a paried t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

Obviously, numerous modifications and variations of the present invention are possible in light of the above teachings. It is therefore to be understood that within the scope of the appended claims, the invention may be practiced otherwise than as specifically described herein.

All of the references cited above are incorporated herein by reference.

What is claimed is:

1. A compound represented by formula (I):

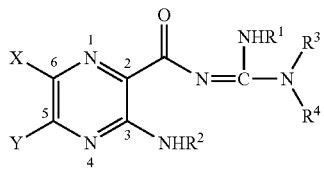
(I)

wherein

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R^2)_2$;

$R^1$ is hydrogen or lower alkyl;

each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

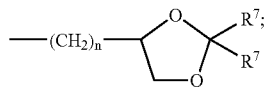

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower alkoxyphenyl)-lower alkyl, naphthyl-lower alkyl, or pyridyl-lower alkyl, with the proviso that at least one of $R^3$ and $R^4$ is a group represented by formula (A):

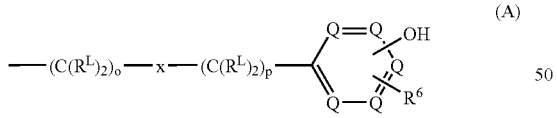
(A)

wherein each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose, or

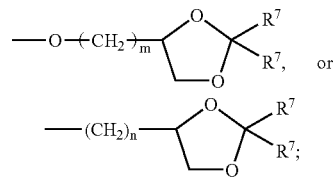

each x is, independently, O, $NR^7$, C=O, CHOH, C=N—$R^6$, or represents a single bond;

each o is, independently, an integer from 0 to 10;

each p is, independently, an integer from 0 to 10;

with the proviso that (a) the sum of o and p in each contiguous chain is from 1 to 10 when x is O, $NR^7$, C=O, or C=N—$R^6$ or (b) that the sum of o and p in each contiguous chain is from 4 to 10 when x represents a single bond;

each $R^6$ is, independently, $-R^7$, $-OH$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

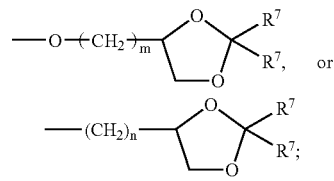

wherein when two $R^6$ are $-OR^{11}$ and are located adjacent to each other on a phenyl ring, the alkyl moieties of the two $R^6$ may be bonded together to form a methylenedioxy group;

each $R^7$ is, independently, hydrogen or lower alkyl;

each $R^8$ is, independently, hydrogen, lower alkyl, $-C(=O)-R^{11}$, glucuronide, 2-tetrahydropyranyl, or

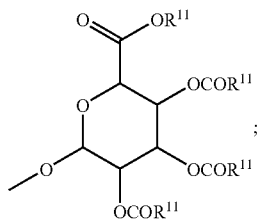

each $R^9$ is, independently, $-CO_2R^7$, $-CON(R^7)_2$, $-SO_2CH_3$, or $-C(=O)R^7$;

each $R^{10}$ is, independently, —H, —SO$_2$CH$_3$, —CO$_2$R$^7$, —C(=O)NR$^7$R$^9$, —C(=O)R$^7$, or —CH$_2$—(CHOH)$_n$—CH$_2$OH;

each Z is, independently, CHOH, C(=O), CHNR$^7$R$^{10}$, C=NR$^{10}$, or NR$^{10}$;

each $R^{11}$ is, independently, lower alkyl;

each g is, independently, an integer from 1 to 6;

each m is, independently, an integer from 1 to 7;

each n is, independently, an integer from 0 to 7;

each Q is, independently, C—R$^6$ or a nitrogen atom, wherein three Q in a ring are nitrogen atoms;

or a pharmaceutically acceptable salt thereof, and inclusive of all enantiomers, diastereomers, and racemic mixtures thereof.

2. The compound of claim 1, wherein Y is —NH$_2$.

3. The compound of claim 2, wherein R$^2$ is hydrogen.

4. The compound of claim 3, wherein R$^1$ is hydrogen.

5. The compound of claim 4, wherein X is chlorine.

6. The compound of claim 5, wherein R$^3$ is hydrogen.

7. The compound of claim 6, wherein each R$^L$ is hydrogen.

8. The compound of claim 7, wherein o is 4.

9. The compound of claim 8, wherein p is 0.

10. The compound of claim 9, wherein x represents a single bond.

11. The compound of claim 10, wherein each R$^6$ is hydrogen.

12. The compound of claim 11, wherein
X is halogen;
Y is —N(R$^7$)$_2$;
R$^1$ is hydrogen or C$_1$–C$_3$ alkyl;
R$^2$ is —R$^7$, —(CH$_2$)$_m$—OR$^7$, or —(CH$_2$)$_n$—CO$_2$R$^7$; R$^3$ is a group represented by formula (A); and
R$^4$ is hydrogen, a group represented by formula (A), or lower alkyl.

13. The compound of claim 12, wherein
X is chloro or bromo;
Y is —N(R$^7$)$_2$;
R$^2$ is hydrogen or C$_1$–C$_3$ alkyl;
at most three R$^6$ are other than hydrogen as defined above; and
at most three R$^L$ are other than hydrogen as defined above.

14. The compound of claim 13, wherein Y is —NH$_2$.

15. The compound of claim 14, wherein
R$^4$ is hydrogen;
at most one R$^L$ is other than hydrogen as defined above; and
at most two R$^6$ are other than hydrogen as defined above.

16. The compound of claim 15, wherein x is O, NR$^7$, C=O, CHOH, or C=N—R$^6$.

17. The compound of claim 15, wherein x represents a single bond.

18. The compound of claim 1, wherein x is O, NR$^7$, C=O, CHOH, or C=N—R$^6$.

19. The compound of claim 1, wherein x represents a single bond.

20. The compound of claim 1, wherein each R$^6$ is hydrogen.

21. The compound of claim 1, wherein at most two R$^6$ are other than hydrogen as defined in claim 1.

22. The compound of claim 1, wherein one R$^6$ is other than hydrogen as defined in claim 1.

23. The compound of claim 1, wherein one R$^6$ is —OH.

24. The compound of claim 1, wherein each R$^L$ is hydrogen.

25. The compound of claim 1, wherein at most two R$^L$ are other than hydrogen as defined in claim 1.

26. The compound of claim 1, wherein one R$^L$ is other than hydrogen as defined in claim 1.

27. The compound of claim 1, wherein x represents a single bond and the sum of o and p is 4 to 6.

28. The compound of claim 1, which is in the form of a pharmaceutically acceptable salt.

29. The compound of claim 1, which is in the form of a hydrochloride salt.

30. The compound of claim 1, which is in the form of a mesylate salt.

31. A pharmaceutical composition, comprising the compound of claim 1 and a pharmaceutically acceptable carrier.

32. A composition, comprising:
the compound of claim 1; and
a P2Y2 receptor agonist.

33. A composition, comprising:
the compound of claim 1; and
a bronchodilator.

34. A method of blocking sodium channels, comprising contacting sodium channels with an effective amount of the compound of claim 1.

* * * * *